US012788023B2

(12) United States Patent
Kickle et al.

(10) Patent No.: US 12,788,023 B2
(45) Date of Patent: Nov. 10, 2026

(54) ENZYMATIC INTRAESTERIFICATION OF NON-TROPICAL PLANT OIL FOR STRUCTURING FOOD SPREADS AND MARGARINE

(71) Applicant: Archer-Daniels-Midland Company, Decatur, IL (US)

(72) Inventors: Bryan Kickle, Mt. Zion, IL (US); Tom Tiffany, Lincoln, IL (US); Mark A. Whitehead, Decatur, IL (US)

(73) Assignee: ARCHER-DANIELS-MIDLAND COMPANY, Decatur, IL (US)

( * ) Notice: Subject to any disclaimer, the term of this patent is extended or adjusted under 35 U.S.C. 154(b) by 843 days.

(21) Appl. No.: 17/791,514

(22) PCT Filed: Jan. 11, 2021

(86) PCT No.: PCT/US2021/012972

§ 371 (c)(1),
(2) Date: Jul. 7, 2022

(87) PCT Pub. No.: WO2021/146145

PCT Pub. Date: Jul. 22, 2021

(65) Prior Publication Data

US 2023/0062018 A1 Mar. 2, 2023

Related U.S. Application Data

(60) Provisional application No. 62/960,373, filed on Jan. 13, 2020.

(51) Int. Cl.
*A23D 7/00* (2006.01)
*A23D 9/04* (2006.01)
(Continued)

(52) U.S. Cl.
CPC ............... *A23D 7/001* (2013.01); *A23D 9/04* (2013.01); *C11C 3/10* (2013.01); *C12P 7/6458* (2022.01)

(58) Field of Classification Search
None
See application file for complete search history.

(56) References Cited

U.S. PATENT DOCUMENTS

2015/0164101 A1* 6/2015 Pan .......................... A23D 9/04
426/601

OTHER PUBLICATIONS

Dubois et al., "Fatty acid Profiles of 80 vegetable oils with regard to their nutritional potential". Euro. J. Lipid Sci. Technol. 109(2007) 710-732 (Year: 2007).*

* cited by examiner

*Primary Examiner* — Erik Kashnikow
*Assistant Examiner* — Assaf Zilbering
(74) *Attorney, Agent, or Firm* — Andrew F. Nilles

(57) ABSTRACT

The present invention relates to a composition comprising a 1,3-selective enzymatic intraesterified oil product having a greater unsaturated-saturated-unsaturated (USU) fatty acid content on the glycerol moiety than the oil from which it was derived. In an embodiment, the starting oil is cottonseed oil and in USU the U is primarily linoleic acid and the S is primarily palmitic acid. Further, the present invention relates to a method for increasing the USU content in an oil, comprising performing 1,3-selective enzymatic intraesterification of a regular starting oil wherein saturated-unsaturated-saturated (SUS) content is greater than the USU content in the starting oil prior to performing 1,3-selective enzymatic intraesterification. Due to the greater USU content, the 1,3-selective enzymatic intraesterified oil product has an increased melting temperature and solid fat content
(Continued)

and therefore useful for margarines and food spreads as compared to the oil it was produced from.

15 Claims, 9 Drawing Sheets

(51) Int. Cl.

| | |
|---|---|
| ***C11C 3/10*** | (2006.01) |
| ***C12P 7/6458*** | (2022.01) |

ENZYMATIC INTRAESTERIFICATION OF NON-TROPICAL PLANT OIL FOR STRUCTURING FOOD SPREADS AND MARGARINE

CROSS-REFERENCE TO RELATED APPLICATIONS

This application is a national stage entry of International Application No. PCT/US21/12972, filed Jan. 11, 2021, which itself claims priority to U.S. Provisional Patent Application No. 62/960,373, filed Jan. 13, 2020, the contents of each are incorporated herein by reference.

FIELD OF THE INVENTION

The present invention relates to an intraesterified non-tropical plant oil triglyceride product, such as an intraesterified cottonseed oil triglyceride product, having increased unsaturated-saturated-unsaturated content than in the non-intraesterified oil from which it was derived.

BACKGROUND OF THE INVENTION

Oils used for food spreads and margarine typically comprise tropical oils, such as palm oil or palm kernel oil, or comprise hydrogenated vegetable oils that are typically blended with other vegetable oils to achieve desired sensory and spreading properties. A disadvantage of tropical oils is that they are derived from forestry plants and are thus not deemed as sustainable as vegetable oils that are derived from annual plants. Another disadvantage of tropical oils is that they are derived from tropical forestry plants that do not commonly grow in non-tropical climates. Conventional processes for modifying natural vegetable oils for use in food products include hydrogenation and interesterfication.

Hydrogenation involves addition of hydrogen to convert unsaturated fatty acids to saturated fatty acids, thereby converting liquid vegetable oils to solids or semi-solids. The addition of hydrogen changes the degree of saturation of fat in the oil, thereby changing the melting range of the oil. The food industry has moved away from partially hydrogenated fats and towards fully hydrogenated fats, interesterified fats, and tropical oils (even though tropical oils have disadvantages as noted in the preceding paragraph).

Interesterification involves blending of at least two different oils so that the fatty acids of these oils are redistributed among the triglycerides of these oils. Interesterification can occur in two ways, i.e., chemical interesterification or enzymatic interesterification. In chemical interesterification, a catalyst, e.g., sodium methoxide, is added to the oils and the triglyceride exchange is initiated with the aid of mild heat and agitation. Chemical interesterification results in random redistribution of fatty acids across glycerol backbones of the triglycerides to create new triglycerides with different solid fat content and melting behaviour. Enzymatic interesterification is a process of using an enzyme, e.g., a lipase, to rearrange the fatty acids of at least two different oils having varying triglycerides to create new triglycerides with different solid fat and melting behaviour.

US 2015/0166932, discloses an intraesterification method in which the fatty acids of the triglycerides of a single high stearic high oleic (HSHO) oil, normally rich in saturated-unsaturated-unsaturated (SUU) type triglycerides, are randomly redistributed between the triglycerides to obtain a fat with an increased amount of saturated-unsaturated-saturated (SUS), saturated-saturated-unsaturated (SSU) type, and saturated-saturated-saturated (SSS) type triglycerides.

U.S. Pat. No. 9,795,152 discloses a 1,3-specific intraesterification method for increasing the SUS content in an oil that is normally rich in saturated-unsaturated-unsaturated (SUU) type triglycerides. The patent discloses that an important characteristic is the oxidative stability of the oil because the oxidation rate of linoleic acid (the main fatty acid in most of the liquid regular seedoils) is 40 times faster than oleic acid. The patent discloses triglycerides in which U (unsaturated fatty acid) is primarily L (linoleic acid) and accordingly commercial fats with this kind of triglyceride have a lower shelf life (or lower rancidity resistance) than those in which U is 0 (oleic acid). The patent therefore discloses that the starting oil or olein fraction is preferably selected from a high stearic high oleic (HSHO) oil. The patent discloses that the main characteristic in these types of oils is that U (unsaturated fatty acid) is primarily O (oleic acid), and this characteristic differentiates this type of oil from regular oils in which the main U is L (linoleic acid). As used herein, a "regular" oil is oil obtained from the most common natural cultivars of oil seed plants as opposed to being derived from special cultivars selected particularly for having an altered triglyceride content.

Spread manufacturers desire base oils with sufficient solids to provide structuring from sources other than tropical oils, such as palm oil, palm oil fractions, interesterified palm oil/palm kernel blends or fully hydrogenated vegetable oil sources.

It would beneficial to have processes and products that do not have the disadvantages of conventional methods and products. For example, it would be beneficial to have an esterification process that uses a single regular or natural non-tropical plant oil as the feedstock to produce a triglyceride product having a melting temperature of at least 75° F. It would be beneficial to have a triglyceride product useful for margarines and food spreads, wherein the main U (unsaturated fatty acid) is L (linoleic acid), and wherein the triglyceride product has increased unsaturated-saturated-unsaturated content than in a regular or natural corresponding oil.

It would beneficial to have processes that do not have the disadvantages of conventional methods. For example, it would be beneficial to have a process that uses a single regular or natural non-tropical oil wherein the main U (unsaturated fatty acid) is L (linoleic acid) to produce a fat with increased solid fat content useful for margarines and food spreads.

SUMMARY

The present invention provides advantages over conventional methods and products. In an aspect, a composition comprises a 1,3-selective enzymatic intraesterified oil product having a greater unsaturated-saturated-unsaturated (USU) content than the oil from which it was derived. As used herein, 1,3-selective enzymatic intraesterified oil product is a composition produced by enzymatic intraesterification of an oil having high saturated-unsaturated-saturated (SUS) content to convert that oil to an intraesterified oil product having greater USU content than the oil from which is was derived by intra-rearrangement of fatty acids at the 1,3 position on the glycerol molecule under conditions that promote acyl migration of saturated fatty acids to the 2 position. In an embodiment, the U is primarily linoleic acid and the S is palmitic acid. In an embodiment, the 1,3-selective enzymatic intraesterified oil product is 1,3-selective enzymatic intraesterified cottonseed oil product. In an embodiment, a 1,3 specific lipase enzyme (e.g., *Thermomyces lanuginosis* (TLIM)) is used for the enzymatic Intraesterification. The 1,3 specific lipase enzyme promotes intra-rearrangement of fatty acids at the 1,3 position on the glycerol molecule. Also during lipase catalyzed re-arrangement, acyl migration to a varying degree will occur, exemplified primarily by migration of palmitic acid to the 2 position.

An objective of the present invention is an intraesterified non-tropical triglyceride product having solid fat content (SFC) at 50° F. that is greater than the basestock from which it was derived. For example, an objective of the present invention is an intraesterified non-tropical triglyceride product having solid fat content (SFC) at 50° F. that is at least ten (10) times greater than the basestock from which it was derived.

In an aspect, a composition comprises an intraesterified non-tropical triglyceride product having solid fat content (SFC) of at least 4% at 50° F., wherein the intraesterified non-tropical triglyceride product is derived from a non-tropical oil. In an aspect, a composition comprises an intraesterified non-tropical triglyceride product having solid fat content (SFC) of at least 7% at 50° F., wherein the intraesterified non-tropical triglyceride product is derived from a non-tropical oil. In an aspect, a composition comprises an intraesterified non-tropical triglyceride product having solid fat content (SFC) of at least 9% at 50° F., wherein the intraesterified non-tropical triglyceride product is derived from a non-tropical oil. In an aspect, a composition comprises an intraesterified non-tropical triglyceride product having solid fat content (SFC) of at least 9.5% at 50° F., wherein the intraesterified non-tropical triglyceride product is derived from a non-tropical oil.

In an aspect, a composition comprises an intraesterified cottonseed triglyceride product having a melting temperature of at least 75° F.

In an aspect, an intraesterified cottonseed triglyceride product has at least 25% more palmitic acid esterified to the second carbon of the glycerol greater than the basestock from which it was derived. In an aspect, the intraesterified cottonseed triglyceride product has at least 12% palmitic acid esterified to the second carbon of the glycerol.

In an aspect, a vegetable oil spread comprises water, an emulsifying agent, and at least 5% by weight of a 1,3-selective enzymatic intraesterified oil product having a greater unsaturated-saturated-unsaturated (USU) content than the oil from which it was derived.

In an aspect, a method comprises increasing the USU content in an oil by performing 1,3-selective enzymatic intraesterification of a natural starting oil wherein SUS content in the oil is greater than the USU content in the starting oil prior to performing 1,3-selective enzymatic intraesterification. In a preferred embodiment, 1,3-selective enzymatic intraesterification is a continuous method.

These and other aspects, embodiments, and associated advantages will become apparent from the following Detailed Description.

DETAILED DESCRIPTION

Figure 1:
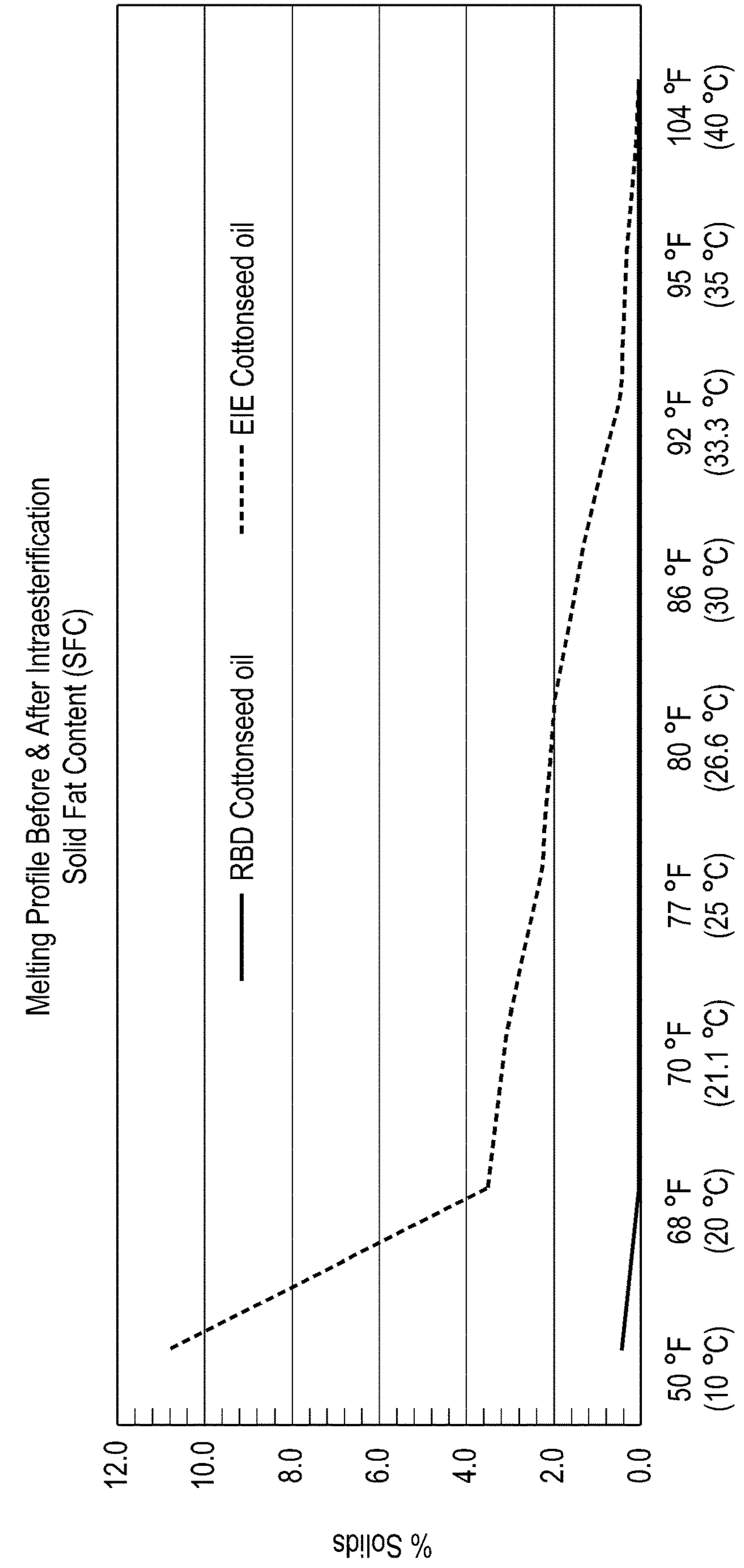
FIG. 1 shows a melting profile (SFC) before and after enzymatic intraesterification (EIE) of cottonseed oil according to aspects of the present invention.

The following acronyms and terms are used in this disclosure.

EIE—Enzymatic Intraesterification. An esterification process that uses a single regular or natural oil and a lipase enzyme to rearrange fatty acids on the glycerol of triglyceride to create new triglycerides with different solid fat content (SFC) and melting behaviour than the single regular or natural oil.

RB cottonseed oil—refined bleached cottonseed oil.

RBD cottonseed oil—refined, bleached and deodorized cottonseed oil.

SFC—solid fat content. The solid fat content is measured by NMR. The solid fat content method determines what percentage of all hydrogen nuclei (protons) in the test sample, composed of hydrogen nuclei in both liquid and solid phases, is due to hydrogen nuclei in the solid phase. This percentage is called the solid fat content.

U—an unsaturated fatty acid (FA).

S—a saturated fatty acid (FA).

SUS—saturated-unsaturated-saturated type triglyceride.

USU—unsaturated-saturated-unsaturated type triglyceride.

MDP—Mettler dropping point. The dropping point of a fat or oil is the temperature at which the test sample will become fluid to flow under the conditions of the test. This is a temperature-related test in which a sample is heated at certain temperature rate until the material flows.

IV—iodine value. The iodine value (or iodine adsorption value or iodine number or iodine index) in chemistry is the mass of iodine in grams that is consumed by 100 grams of a chemical substance. Iodine numbers are often used to determine the amount of unsaturation in fatty acids. The iodine value can also be calculated by fatty acid composition.

GLC—gas liquid chromatography.

FAC—Fatty acid composition. This measure determines the fatty acid present in an oil or fat.

ROC—rate of crystallization (the rate at which a fat or oil crystalizes at a certain temperature as measured by SFC).

Palmitic acid—a sixteen carbon containing fatty acid. Palmitic acid is a saturated fatty acid.

Stearic acid—an eighteen carbon containing fatty acid. Stearic acid is a saturated fatty acid.

Oleic acid—an eighteen carbon containing fatty acid with one double bond. Oleic acid is an unsaturated fatty acid.

Linoleic acid—an eighteen carbon containing fatty acid with two double bonds. Linoleic acid is an unsaturated fatty acid.

Linolenic acid—an eighteen carbon containing fatty acid with three double bonds. Linoleic acid is an unsaturated fatty acid. Linolenic acid is an unsaturated fatty acid.

Triglyceride—an ester formed from glycerol and three fatty acids attached to glycerol through an ester linkage. The fatty acids are attached at the sn-1, sn-2, and sn-3 positions.

sn-2—the position of the fatty acid in the middle position or 2 position of the triglyceride.

TLIM—the lipase enzyme known as *Thermomyces lanuginosis.*

A process is disclosed herein for the production of a 1,3-selective enzymatic intraesterified oil product having a greater unsaturated-saturated-unsaturated (USU) content than the starting oil from which it was derived or produced from. In an embodiment, the 1,3-selective enzymatic intraesterification is a continuous process. In an embodiment, the U is primarily linoleic acid and the S is palmitic acid. The 1,3-selective enzymatic intraesterified oil product may be used as a base oil for the production of water-in-oil spreads and margarines, including but not limited to tub based water-in-oil food spreads and margarines. Those skilled in the art will recognize that margarine is no less than 80% fat or oil. whereas a food spread or other food application may have less than 80% fat or oil. The 1,3-selective enzymatic intraesterified oil product disclosed herein is derived from non-tropical oil and non-hydrogenated vegetable oil sources. The process and 1,3-selective enzymatic intraesterified oil product of the present invention have advantages over conventional methods and conventional oils derived from and tropical oils and hydrogenated vegetable oil sources.

In an embodiment, the 1,3-selective enzymatic intraesterified oil product of the present invention is derived from cottonseed oil. Cottonseed oil does not have the same sustainability issues as tropical oils derived from tropical trees, such as palm oil. Cottonseed oil does not have the same health issues that have been raised by others in connection with use of partially hydrogenated vegetable oils.

In an embodiment, the 1,3-selective enzymatic intraesterified oil product of the present invention has an increased level of solid fat content as compared to the oil from which it is derived.

Those of ordinary skill in the art having the benefit of the present disclosure will recognize that the 1,3-selective enzymatic intraesterified oil product of the present invention may be used as a base oil in food spreads, margarines, panfrying products, and the like. The 1,3-selective enzymatic intraesterified oil products of the present invention may be used as an oil component in other food applications, including but not limited to meat alternatives, frozen food coatings, and frozen food novelty products.

Turning to further description of the invention, in an aspect, a method comprises increasing the USU content in an oil by performing continuous 1,3-selective enzymatic intraesterification (EIE) of a natural starting oil wherein SUS content in the oil is greater than the USU content in the starting oil prior to performing 1,3-selective enzymatic intraesterification.

In accordance with aspects of the invention, cottonseed oil has been enzymatically intraesterified to successively rearrange the starting material to produce a base oil with a solid fat content increase capable of providing enough solid fat for use in spreads or margarine.

In accordance with aspects of the invention, a process comprises 1,3-selective enzymatic intraesterification using a lipase enzyme. In an embodiment, the lipase enzyme comprises *Thermomyces lanuginosis* (TLIM).

In accordance with aspects of the invention, intraesterified cottonseed oil was produced utilizing a bench top intrasterification process in which cottonseed oil was passed through a column containing an immobolized 1,3 specific lipase enzyme (TLIM in this example) that promotes intra-rearrangement of fatty acids at the 1,3 position on the glycerol molecule. Also during lipase re-arrangement, acyl migration to a varying degree does occur, as exemplified by the migration of palmitic acid to the sn-2 position. More specifically, intraesterified cottonseed oil was produced utilizing a bench top process by placing 267 grams of TLIM enzyme (manufactured by Novozymes A/S, Denmark) in a heated water jacketed glass chromatography column that served as a fixed bed reactor. The lipase enzyme was slurried with cottonseed oil to aid in the adding of the enzyme to the fixed bed reactor. Cottonseed oil was then added to a reservoir and heated to 70° C. The cottonseed oil was then pumped with the utilization of a piston pump to the top of the fixed bed reactor of lipase enzyme at a designated flow rate of 727 grams per hour to pass the cottonseed oil through the column bed containing the enzyme. The column of enzyme was maintained at 70° C. with the aid of a heated water jacket. As the cottonseed oil came into contact with the lipase enzyme, intra-rearrangement of the cottonseed oil fatty acids occurred. With the rearrangement of the cottonseed oil, new triglycerides were produced, thus modifying the physical properties of cottonseed oil to yield an increase in the solid fat content (SFC), melting point and palmitic acid in the sn-2 position. The cottonseed oil was continuously pumped through the fixed bed reactor to yield the amount of intraesterified cottonseed oil for characterization and small scale spread production using a scraped surface heat exchanger (manufactured by Armfield Limited, United Kingdom).

Figure 9:
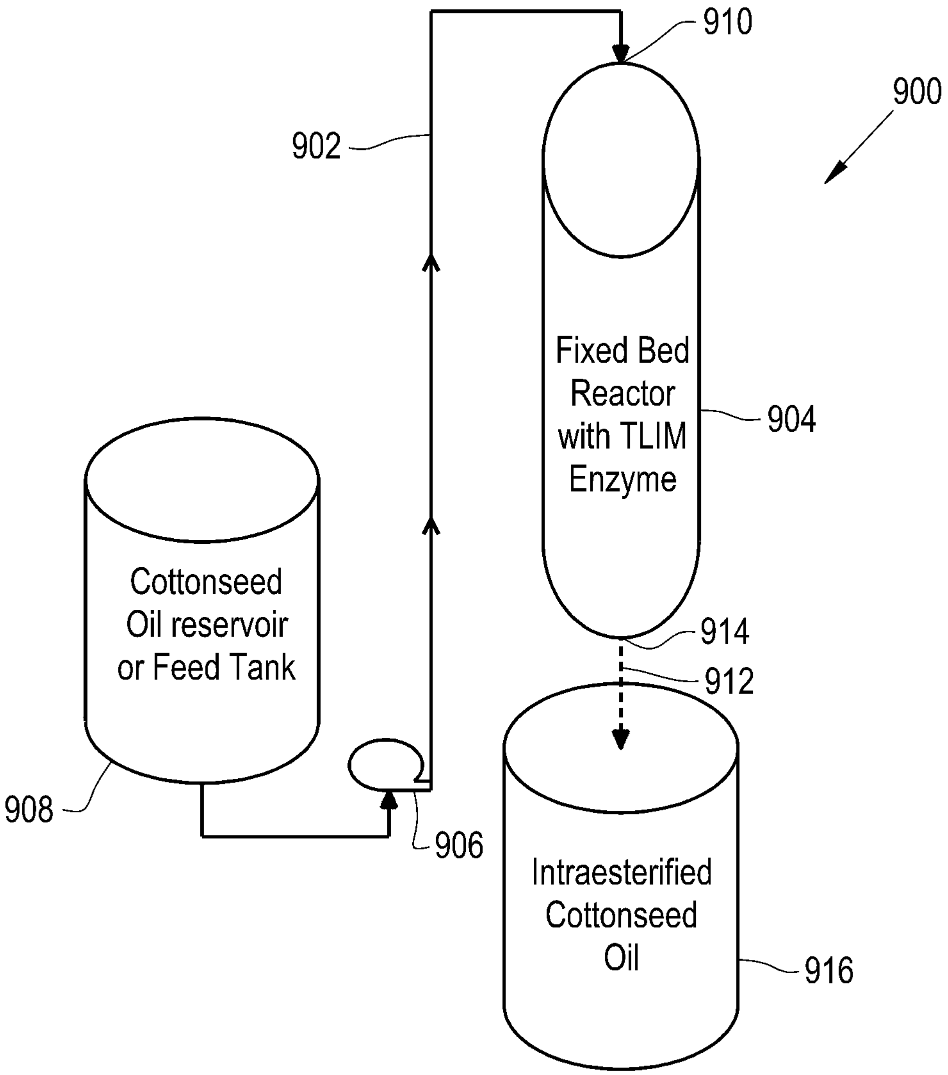
FIG. 9 is a flow diagram depicting production of intraesterified cottonseed oil in accordance with aspects of the invention.

FIG. 9 is a process flow diagram depicting intraesterification process 900 for production of intraesterified cottonseed oil in accordance with aspects of the invention. As shown in FIG. 9, intraesterification process 900 comprises conveying cottonseed oil 902 to a fixed bed reactor 904 comprising a 1,3 selective lipase enzyme, e.g., TLIM enzyme. Cottonseed oil 902 may be conveyed by pump 906 from cottonseed oil feed source 908, e.g., a cottonseed oil reservoir or feed tank, to fixed bed reactor 904. As shown in FIG. 9, cottonseed oil may be held or maintained in cottonseed oil feed source 908 at a temperature greater than ambient temperature, e.g., 70° C. Cottonseed oil 902 may enter fixed bed reactor 904 through inlet port 910 of fixed bed reactor 904. Inlet port 910 may be located at the top of fixed bed reactor 904. The flow rate of cottonseed oil 902 conveyed to fixed bed reactor 904 may be at a predetermined flow rate, e.g., 727 grams/hour. The amount of enzyme in fixed bed reactor 904 may be a predetermined amount, e.g., 267 grams of enzyme. The ratio of the flow rate of cottonseed oil 902 conveyed to fixed bed reactor 904 to the amount of enzyme in fixed bed reactor 904 may be a predetermined ratio, e.g., 727 grams/hour of cottonseed oil 902 to 267 grams of enzyme, i.e., 2.72. The temperature in fixed bed reactor 904 may be maintained at a temperature greater than ambient temperature, e.g., 70° C. In fixed bed reactor 904, cottonseed oil 902 is converted to intraesterified cottonseed oil 912. Intraesterified cottonseed oil 912 may exit fixed bed reactor 904 through outlet port 914 of fixed bed reactor 904. Outlet port 914 may be located at the bottom of fixed bed reactor 904. Intraesterified cottonseed oil 912 may be conveyed from fixed bed reactor 904 to intraesterified cottonseed oil product tank 916.

Crystallization trials were run to produce a 60% fat based spread. Two different lots of enzymatically intraesterified cottonseed oil were successful in producing a stable under-refrigeration 60% fat based spread. Water in oil emulsions were produced in the following manner. Intraesterified cottonseed oil was added to a stainless steel container and heated to 60° C. Distilled monoglycerides and lecithin were then added to assist in water in oil emulsification. Water was added to a separate stainless steel container and warmed, and salt was added to the water and stirred until dissolved in the water. The water with dissolved salt was then slowly added to the intraesterified cottonseed oil containing the emulsifiers. The mixture was then heated and agitated to ensure homogeneity. The water in oil emulsion was then passed through a scraped surface heat exchanger (manufactured by Armfield Limited, United Kingdom) to initiate crystallization. The emulsion was then passed through two scraped surface heat exchange barrels and one pinworking barrel to produce a homogeneous water in oil 60% fat spread. The two scraped surface heat exchangers barrels were chilled to between 4° C.-10° C. to initiate lipid crystallization, whereas the pinworking barrel was not cooled, to allow for crystal growth and even distribution of lipid crystal. The use of a scraped surface heat exchanger is a common practice to evaluate a variety of basestocks that can be used in water in oil spread formulations.

Table 1 provides an analysis of basestock cottonseed oil and enzymatically intraesterified (EIE) cottonseed oil derived from the basestock cottonseed oil. As shown in Table 1, intraesterified RBD cottonseed oil had 10.72% SFC at 50° C., whereas the basestock RBD cottonseed oil from which it was derived had 0.43% SFC at 50° C.

As shown in Table 1, intraesterified RBD cottonseed oil had 2-monopalmitin (i.e., palmitic acid linked to the 2 position of glycerol) at 19.35% by weight, whereas the basestock RBD cottonseed oil from which it was derived had 2-monopalmitin at 2.46% by weight. Thus, the oil was converted from an oil that was SUS to an oil that was USU by the 1,3 selective lipase.

Table 1 shows the FAC profile of intraesterified RBD cottonseed oil and the basestock RBD cottonseed oil from which it was derived is set forth in the row beginning with "Myristic C14:0" through "Total Saturated FAs."

FIG. 1 is a graph of data set forth in Table 1, depicting the melting profile before and after enzymatic intraesterification (EIE) of RBD cottonseed oil, as characterized by % solids versus temperature.

TABLE 1

| Analysis | Basestock Before Intraesterification RBD Cottonseed Oil (CSO) 5995-67 | Intraesterified RBD Cottonseed Oil (CSO) 5995-67 |
|---|---|---|
| Mettler Drop Point (F.) | 51.44 | 82.40 |
| Iodine Value (IV) by GLC | 110.2 | 110.4 |
| SFC @ 50° F. (10 C.) | 0.43 | 10.72 |
| SFC @ 68° F. (20 C.) | 0.00 | 3.49 |
| SFC @70° F. | 0.00 | 3.07 |
| SFC @ 77° F. (25 C.) | 0.00 | 2.30 |
| SFC @ 80° F. | 0.00 | 2.01 |
| SFC @ 86° F. (30 C.) | 0.00 | 1.38 |
| SFC @ 92° F. | 0.00 | 0.49 |
| SFC @95° F. (35 C.) | 0.00 | 0.30 |
| SFC @ 104° F. (40 C.) | 0.00 | 0.00 |
| Lovibond Color (Y) | | 34.00 |
| Lovibond Color (R) | | 2.00 |
| Diacylglycerol (DAG) | 2.35 | 3.66 |
| 2-MonoMyristin | 0.54 | 1.11 |
| 2-MonoPalmitin | 2.46 | 19.35 |
| 2-MonoStearin | 0.32 | 1.97 |
| 2-MonoOlein | 19.92 | 17.11 |
| 2-MonoLinolenin | 75.47 | 60.15 |
| 2-MonoArachidin | 0.12 | 0.22 |
| Myristic C14:0 | 0.81 | 0.81 |
| Palmitic C16:0 | 22.99 | 22.94 |
| Palmitoleic C16:1 | 0.55 | 0.56 |
| Stearic C18:0 | 2.56 | 2.55 |
| Total C18:1 trans FA | 0.23 | 0.12 |
| Total C18:1 cis FA | 16.99 | 17.09 |
| Total C18:2 trans FA | 0.78 | 0.96 |
| Total C18 2 cis FA | 53.55 | 53.40 |
| Total C18:3 trans FA | 0.03 | 0.05 |
| Total C18:3 cis FA | 0.24 | 0.26 |
| Arachidic C20:0 | 0.29 | 0.28 |
| Linolenic C18:3n3cis | 0.19 | 0.18 |
| Behenic C22:0 | 0.14 | 0.14 |
| Lignoceric C24:0 | 0.08 | 0.09 |
| Total trans FA | 1.05 | 1.13 |
| Total Saturated FAs | 27.02 | 26.96 |

Table 2 provides the formula for a 60% fat spread with EIE cottonseed oil. 90% Distilled Alpha Mono and soy lecithin are emulsifiers. In this example, the 90% distilled alpha mono was Alphadim 90 SBK, and the soy lecithin was Yelkin SS. Natural beta carotene was included in the fat spread formula to provide yellow coloring so that the spread had color more similar to butter than without the addition of the natural beta carotene.

TABLE 2

| 60% Fat Spread Formula | |
|---|---|
| Fat Phase % by weight | Water Phase % by weight |
| 59.2990% Intraesterified Cottonseed Oil | 38.7% Water |
| 0.5000% 90% Distilled Alpha Mono | 1.3000% Salt |
| 0.2000% Soy Lecithin | |
| 0.0010% Natural Beta Carotene | |
| 60% Total | 40% Total |

Those skilled in the art, having the benefit of this disclosure, will recognize the attributes of the base stock and the above 60% fat spread with EIE cottonseed oil derived therefrom: (i) no palm or other tropical oil; (ii) no hydrogenation; (iii) moderate in saturates (around 25-28% saturates versus around 50% saturates in palm and other tropical oils); and (iv) good source of linoleic oil, an omega-6 essential fat.

Table 3 provides an analysis of basestock cottonseed oil and enzymatically intraesterified (EIE) cottonseed oil derived from the basestock cottonseed oil. As shown in Table 3, the cottonseed oil basestock had a SFC of 0.32% at 50° F. and 2-monopalmitin of only 2.10% in the 2-position of the triglyceride, whereas EIE undeodorized cottonseed oil produced on different collection dates 1 through 8 (i.e., "Collect 1, Collect 2, etc.") from the basestock in accordance with aspects of the present invention had SFC at 50° F. ranging from 10.93% (Collect 2) to 9.63% (Collect 7) and 2-monopalmitin in the 2-position of the triglyceride ranging from 18.68% (Collect 1) to 17.66% (Collect 5). When EIE undeodorized cottonseed oil produced on the different collection dates 1 through 8 were combined in equal amounts as an "all eight runs homogeneous" sample, that "all eight runs homogeneous" sample had SFC of 10.98% at 50° F. and 2-monopalmitin in the 2-position of the triglyceride of 18.00%. When the "all eight runs homogenous" sample of EIE undeodorized cottonseed oil produced on different collection dates was then deodorized, the deodorized all collects sample had SFC of 10.23% at 50° F. and 2-monopalmitin in the 2-position of the triglyceride of 17.90%.

TABLE 3

| Analytical | Basestock RBD CSO Lot# 012218D 5995-98 | Intraesterified CSO Undeodorized Large Bench Collect 1 Homog 5995-98 | Intraesterified CSO Undeodorized Large Bench Collect 2 Homog 5995-98 | Intraesterified CSO Undeodorized Large Bench Collect 3 Homog 5995-98 | Intraesterified CSO Undeodorized Large Bench Collect 4 Homog 5995-98 | Intraesterified CSO Undeodorized Collect 5 Homog 5995-98 |
|---|---|---|---|---|---|---|
| Mettler Drop Point (F.) | 48.92 | 83.48 | 81.50 | 83.66 | 80.24 | 81.50 |
| IV by GLC | 112.1 | | | | | |
| SFC @ 50° F. (10 C.) | 0.32 | 10.46 | 10.93 | 10.46 | 10.04 | 10.11 |
| SFC @ 68° F. (20 C.) | 0.13 | 3.16 | 3.54 | 3.19 | 3.46 | 3.09 |
| SFC @ 70° F. | 0.10 | 3.01 | 3.06 | 3.04 | 2.93 | 2.66 |
| SFC @ 77° F. (25 C.) | 0.00 | 1.87 | 2.20 | 2.06 | 2.13 | 2.33 |
| SFC @ 80° F. | 0.00 | 1.69 | 1.68 | 1.73 | 1.57 | 1.51 |
| SFC @ 86° F. (30 C.) | 0.00 | 1.38 | 1.33 | 1.08 | 1.18 | 1.10 |
| SFC @ 92° F. | 0.00 | 0.75 | 0.79 | 0.82 | 0.50 | 0.43 |
| SFC @ 95° F. (35 C.) | 0.00 | 0.37 | 0.27 | 0.05 | 0.17 | 0.15 |
| SFC @ 104° F. (40 C.) | 0.00 | 0.08 | 0.04 | 0.00 | 0.00 | 0.00 |
| 2-MonoMyristin | 0.00 | 1.27 | 1.35 | 1.67 | 1.44 | 1.52 |
| 2-MonoPalmitin | 2.10 | 18.68 | 18.19 | 18.13 | 17.87 | 17.66 |
| 2-MonoStearin | 1.90 | 0.00 | 2.11 | 2.02 | 1.74 | 1.25 |
| 2-MonoOlein | 18.05 | 18.38 | 16.12 | 16.10 | 16.54 | 16.91 |
| 2-MonoLinolein | 77.01 | 60.97 | 61.51 | 61.19 | 61.48 | 61.77 |
| 2-MonoLinolenin | 0.76 | 0.37 | 0.40 | 0.52 | 0.47 | 0.53 |
| 2-MonoArachidin | 0.18 | 0.33 | 0.33 | 0.37 | 0.36 | 0.35 |
| Myristic C14:0 | 0.81 | 0.81 | | | | |
| Palmitic C16:0 | 22.39 | 22.25 | | | | |
| Palmitoleic C16:1 | 0.56 | 0.56 | | | | |
| Stearic C18:0 | 2.39 | 2.37 | | | | |
| Total C18:1 trans FA | 0.29 | 0.31 | | | | |
| Total C18:1 cis FA | 16.48 | 16.52 | | | | |
| Total C18:2 trans FA | 0.69 | 0.68 | | | | |
| Total C18 2 cis FA | 55.11 | 55.18 | | | | |
| Total C18:3 trans FA | 0.00 | 0.01 | | | | |
| Total C18:3cis FA | 0.18 | 0.22 | | | | |
| Arachidic C20:0 | 0.26 | 0.27 | | | | |
| Gadoleic C20:1n9 cis | 0.07 | 0.07 | | | | |
| Behenic C22:0 | 0.12 | 0.13 | | | | |
| Lignoceric C24:0 | 0.07 | 0.09 | | | | |
| Total trans FA | 0.98 | 1.00 | | | | |
| Total Saturated FAs | 26.17 | 26.05 | | | | |

| Analytical | Intraesterified CSO Undeodorized Large Bench Collect 6 Homog 5995-98 | Intraesterified CSO Undeodorized Large Bench Collect 7 Homog 5995-98 | Intraesterified CSO Undeodorized Large Bench Collect 8 Homog 5995-98 | Intraesterified CSO Undeodorized Large Bench All Eight Runs Homogenous 5995-98 | Intraesterified CSO Deodorized Large Bench All Eight Runs Homogenous 5995-98 |
|---|---|---|---|---|---|
| Mettler Drop Point (F.) | 82.76 | 81.32 | 82.94 | 82.04 | 81.14 |
| IV by GLC | | | | 112.3 | 111.6 |
| SFC @ 50° F. (10 C.) | 10.22 | 9.63 | 10.02 | 10.98 | 10.23 |
| SFC @ 68° F. (20 C.) | 3.28 | 3.16 | 3.05 | 3.21 | 3.22 |
| SFC @ 70° F. | 2.93 | 2.83 | 2.76 | 2.93 | 2.93 |
| SFC @ 77° F. (25 C.) | 2.28 | 1.90 | 2.16 | 2.11 | 2.15 |
| SFC @ 80° F. | 2.02 | 1.49 | 1.78 | 1.86 | 1.83 |
| SFC @ 86° F. (30 C.) | 1.28 | 1.02 | 1.17 | 1.20 | 1.28 |
| SFC @ 92° F. | 0.46 | 0.57 | 0.82 | 0.81 | 0.72 |
| SFC @ 95° F. (35 C.) | 0.11 | 0.12 | 0.38 | 0.18 | 0.31 |
| SFC @ 104° F. (40 C.) | 0.00 | 0.11 | 0.00 | 0.00 | 0.00 |
| 2-MonoMyristin | 1.92 | 1.32 | 1.38 | 1.27 | 1.54 |
| 2-MonoPalmitin | 17.76 | 18.30 | 17.88 | 18.00 | 17.90 |
| 2-MonoStearin | 1.72 | 1.24 | 1.35 | 2.01 | 1.53 |
| 2-MonoOlein | 16.51 | 16.97 | 16.91 | 16.27 | 16.72 |
| 2-MonoLinolein | 61.66 | 61.34 | 61.74 | 61.79 | 61.60 |
| 2-MonoLinolenin | 0.44 | 0.47 | 0.51 | 0.47 | 0.53 |
| 2-MonoArachidin | 0.00 | 0.36 | 0.23 | 0.19 | 0.20 |

TABLE 3-continued

| | | | |
|---|---|---|---|
| Myristic C14:0 | 0.80 | 0.80 | 0.81 |
| Palmitic C16:0 | 22.30 | 22.33 | 22.32 |
| Palmitoleic C16:1 | 0.57 | 0.57 | 0.56 |
| Stearic C18:0 | 2.37 | 2.39 | 2.55 |
| Total C18:1 trans FA | 0.29 | 0.28 | 0.19 |
| Total C18:1 cis FA | 16.50 | 16.48 | 16.80 |
| Total C18:2 trans FA | 0.67 | 0.70 | 0.85 |
| Total C18 2 cis FA | 55.07 | 55.13 | 54.47 |
| Total C18:3 trans FA | 0.00 | 0.01 | 0.02 |
| Total C18:3cis FA | 0.25 | 0.22 | 0.22 |
| Arachidic C20:0 | 0.27 | 0.28 | 0.28 |
| Gadoleic C20:1n9 cis | 0.07 | 0.08 | 0.07 |
| Behenic C22:0 | 0.14 | 0.13 | 0.15 |
| Lignoceric C24:0 | 0.08 | 0.09 | 0.07 |
| Total trans FA | 0.96 | 0.98 | 1.06 |
| Total Saturated FAs | 26.12 | 26.15 | 26.35 |

Table 4 shows a residence time study depicting the impact of residence time on SFC and C16:0 sn-@. The designation 1× Decrease Residence means the residence time of the EIE cottonseed oil in the vessel was reduced in half (50%) from the regular residence time by reducing the amount of enzyme in the vessel by half (50%). The designation 2× Decrease Residence means the residence time of the EIE cottonseed oil in the vessel was reduced in half again from 1× Decrease Residence so the residence time was 25% of the regular residence time by reducing the amount of enzyme in the vessel by half again (25% enzyme compared to 100% enzyme used for the regular residence time). The residence time may also be referred to as retention time. With respect to Table 4, the regular residence time was 30.08 minutes, the 1× Decrease residence time was 15.03 minutes, and the 2× Decrease Residence Time was 7.49 minutes. These same residence times are identified in Table 5, discussed below. As shown in Table 4, reducing the residence time by 50% by reducing the amount of enzyme in the vessel by 50% resulted in a reduction of 16:0 sn-2, i.e., palmitic acid, fatty acid in the 2-position of the triglyceride from 19.35% to 12.29%. This value of 12.29% is greater than the 2.46% (see Tables 1 and 4, row for 2-MonoPalmitin) or 2.10% (see Table 3, row for 2-MonoPalmitin) for basestock RBD cottonseed oil (CSO). An objective of the present invention is an EIE product having an SFC at 50° F. greater than the basestock the EIE product was derived from. An objective of the present invention is an EIE product having an SFC at 50° F. at least ten (10) times greater than the basestock the EIE product was derived from.

Figure 2:
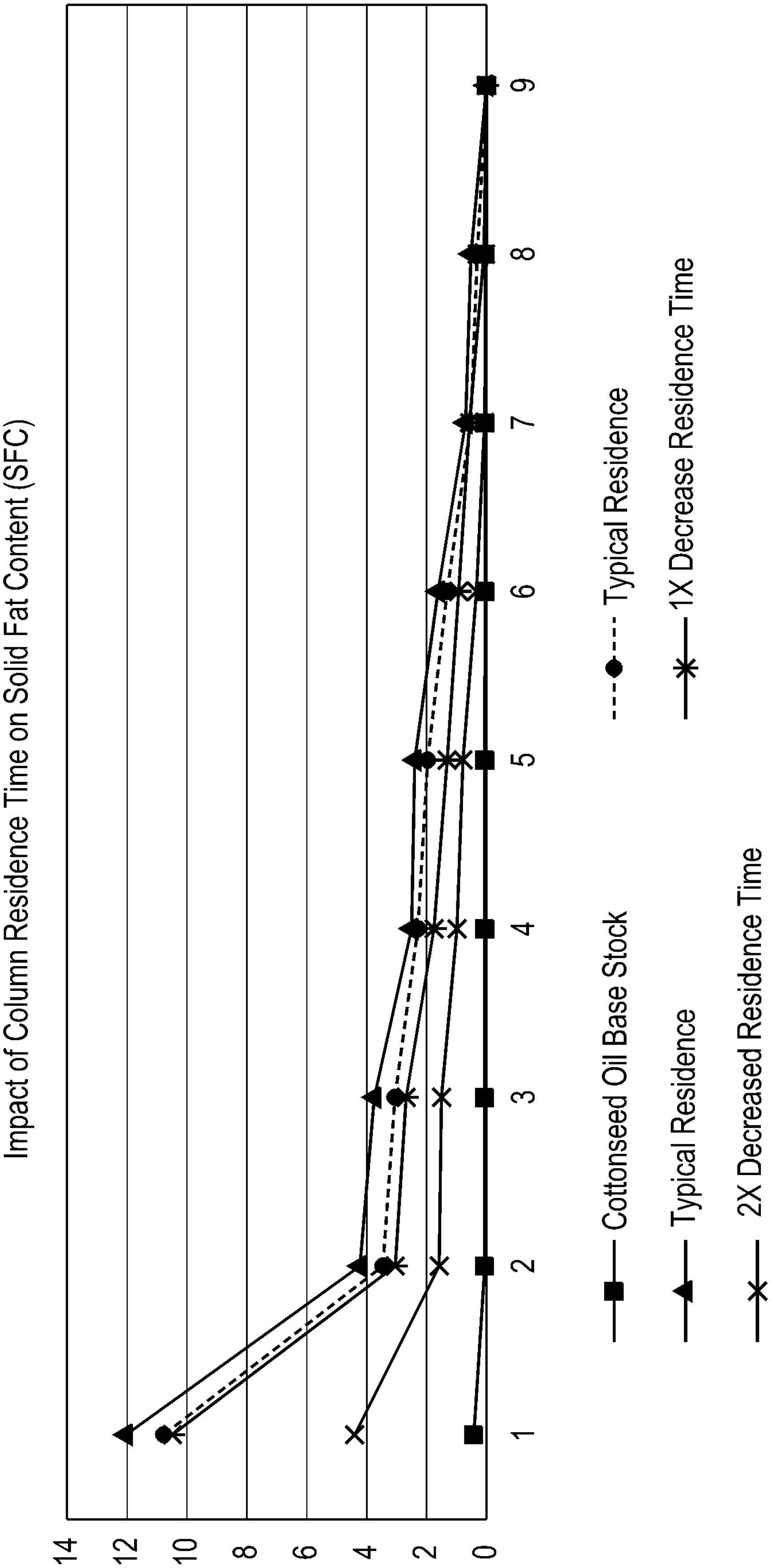
FIG. 2 shows impact of residence time on solid fat content (SFC) according to aspects of the present invention.

FIG. 2 is a graph of the data set forth in Table 4, showing the impact of residence time on SFC.

In an embodiment, an EIE product has an SFC at 50° F. of at least 4.0% at 50° F. for spreadability functionality. As shown in Table 4, a 2× Decrease Residence Time (for Collection Date 1), i.e., only 25% residence time/25% enzyme than regular residence time/enzyme amount, resulted in an SFC of 4.39% at 50° F. The basestock from which this EIE product was derived had an SFC of 0.32% (see Table 3). Thus, in this embodiment of the present invention, the EIE product had 13.7 times greater SFC than the basestock from which it was derived.

In a preferred embodiment, the EIE of the present invention has an SFC of at least 9.0% at 50° F. In a more preferred embodiment, the EIE of the present invention has an SFC of at least 9.50% at 50° F. As shown in Table 4, a 1× Decrease Residence Time (for Collection Date 1) resulted in an SFC of 10.45% at 50° F. A 50% residence time, i.e., reducing the amount of enzyme in the vessel by 50%, surprisingly provides an EIE cottonseed oil having excellent spreadability functionality and is not much less than the SFC of 10.72% at 50° F. for an EIE cottonseed oil under regular residence time, i.e., a regular amount of enzyme. The above SFC of 10.45% (1× Decrease Residence Time) and 10.72% (regular residence time) at 50° F. for EIE cottonseed oil is relatively close to SFC of about 12-15% at 50° F. for interesterified blend of palm oil and palm kernel blends commonly used in the margarine and spreads industry.

TABLE 4

| Analysis | Cotton-seed Oil Base Stock | Regular Residence | Regular Residence | 1 X Decrease Residence Time | 2X Decreased Residence Time |
|---|---|---|---|---|---|
| SFC @ 50 F. | 0.43 | 10.72 | 11.97 | 10.45 | 4.39 |
| SFC @ 68 F. | 0.00 | 3.49 | 4.19 | 3 | 1.62 |
| SFC @ 70 F. | 0.00 | 3.07 | 3.78 | 2.7 | 1.55 |
| SFC @ 77 F. | 0.00 | 2.3 | 2.6 | 1.78 | 1 |
| SFC @ 80 F. | 0.00 | 2.01 | 2.42 | 1.36 | 0.84 |
| SFC @ 86 F. | 0.00 | 1.38 | 1.67 | 0.98 | 0.39 |
| SFC @ 92 F. | 0.00 | 0.49 | 0.78 | 0.58 | 0.1 |
| SFC @ 95 F. | 0.00 | 0.3 | 0.56 | 0.05 | 0.04 |
| SFC @ 104 F. | 0.00 | 0 | 0 | 0 | 0 |
| 16:0 sn-2 | 2.46 | 19.35 | 20 | 12.29 | 2.67 |
| Total Saturated Fatty Acids (FAs) | 27.02 | 26.96 | 27.63 | 27.62 | 28.33 |

Figure 3:
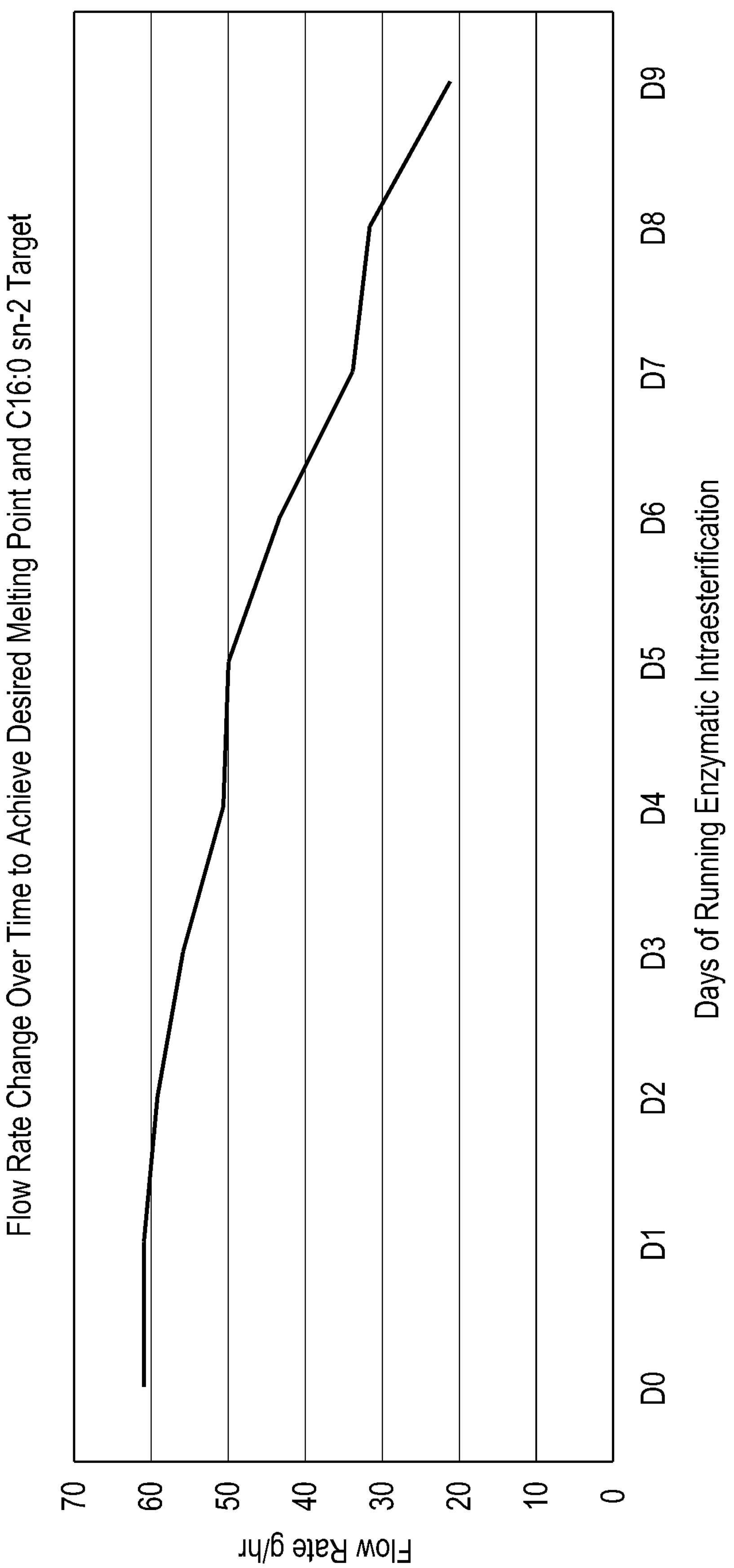
FIG. 3 shows flow rate change over first half-life of TLIM enzyme for a target Mettler dropping point ("MDP") of 82-83 degrees Fahrenheit with certain reaction conditions according to aspects of the present invention, including desired C16:0 sn-2 target.

FIG. 3 shows flow rate change over first half-life of TLIM enzyme for a target Mettler dropping point ("MDP") of 82-83 degrees Fahrenheit with certain reaction conditions according to aspects of the present invention. In the half-life test, TLIM enzyme was loaded into a heat-jacketed column, and basestock cottonseed oil was passed through the enzyme bed to facilitate continuous enzymatic intraesterification, and the intraesterified cottonseed oil product was then analysed. The MDP and flow rate through the column was measured daily. In the example shown in FIG. 3, the column set-up comprised a TLIM load of 24 grams, a reaction temperature of 70° C., feedstock consisting of RBD cottonseed oil, and the following reaction targets: flow rate began at 60 grams/hour, 82-83° F. MDP, and 17-19% sn-2 monopalmitin. The following observations were made: (i) the $1^{st}$ half-life=rate of reaction slowed by 50%, 30 grams/hour, to achieve the MDP target; (ii) the $2^{nd}$ and $3^{rd}$ half-life was determined by the time taken to reduce flow by 75% and 87%. In an embodiment, a column in a production plant may be run to the $3^{rd}$ half-life effectively to utilize the enzyme.

The half-life test indicates the (i) effect of oil type and quality on enzymatic reaction efficiency; (ii) how long the enzyme will work to meet reaction targets; and (iii) the amount of oil reacted per gram of enzyme.

Table 5 shows the run conditions for producing intraesterified cottonseed oil in accordance with aspects of the invention. The samples produced were identified as 5995-105, 5995-110, 5995-116, and 5995-67. The run conditions for producing intraesterified cottonseed oil sample 5995-67 was substantially similar to the run conditions for producing intraesterified cottonseed oil sample 5995-105.

TABLE 5

| | Blend | | |
|---|---|---|---|
| ID | CSO Large Bench Regular Flow EIE DEOD CSO, Large Bench Final Combined Large Bench Deod 15 gal. Homog of Collect 1, 2, 3 5995-105 | CSO Large Bench Fast Flow EIE DEOD CSO, Large Bench Collect 1, Fast Flow (~4.5 gal. produced) 5995-110 | CSO Large Bench Double -Fast Flow EIE DEOD CSO, Large Bench Collect 1, Double Fast Flow 5995-116 |
| Ml/Min (Optos 1HM pump) | 14.55 ml/min | 14.55 ml/min | 14.55 ml/min |
| Enzyme | TLIM | TLIM | TLIM |
| Column Temperature | 70° F. | 70° F. | 70° F. |
| Actual Grams/Hour | 727.41 | 727.82 | 730.66 |
| Actual Ml/Hour | 799.35 | 799.80 | 802.92 |
| Enzyme Bulk Density (g/ml) | 0.40 | 0.40 | 0.40 |
| Enzyme Void Space (g/ml) | 0.60 | 0.60 | 0.60 |
| Amount Enzyme (g) | 267.16 | 133.58 | 66.79 |
| Oil Density (ml/g) | 0.91 | 0.91 | 0.91 |
| Retention Time (minutes) | 30.08 | 15.03 | 7.49 |

Table 6 shows the impact of cotton stearin addition post intraesterification to EIE deodorized CSO made in accordance with the present invention under regular flow (residence time). As shown in Table 6, the addition of stearin provides increased SFC % at 50° F. to EIE deodorized CSO as compared to an EIE cottonseed oil devoid of stearin. For example, an EIE deodorized CSO made in accordance the present invention having 10.72% SFC % at 50° F. without stearin was increased by (i) 16.5% to 12.84% SFC at 50° F. by adding 3% CSO stearin, (ii) 23.4% to 13.99% SFC at 50° F. by adding 5% CSO stearin, and (iii) 29.7% to 15.25% SFC at 50° F. by adding 7% CSO stearin. In another example, an EIE deodorized CSO made in accordance the present invention having 11.97% SFC at 50° F. without stearin was increased by (i) 18% to 14.59% SFC % at 50° F. by adding 3% CSO stearin, (ii) 24.9% to 15.94% SFC at 50° F. by adding 5% CSO stearin, and (iii) 29.54% to 16.99% SFC at 50° F. by adding 7% CSO stearin. Those skilled in the art having the benefit of the present disclosure will recognize that the present invention allows for production of an EIE cottonseed oil having a specific predetermined target SFC % at 50° F. by addition of stearin. The ability to fine tune production of an EIE cottonseed oil having a specific predetermined target SFC % at 50° F. is useful to meet the needs of manufacturers of margarines and spreads.

TABLE 6

| | Regular Flows 10.72 SFC@50 F. Start | | | |
|---|---|---|---|---|
| Analysis | NO ADD EIE Deod CSO Large Bench 3rd Trial Collection 1 Homog 5-gal 5995-67 | 3% CSO Stearin 97% EIE Cottonseed Oil Base Oil 5995-67 Typical Flow (10.72 SFC@50 F.): 3% Cottonseed Oil Stearin | 5% CSO Stearin 95% EIE Cottonseed Oil Base Oil 5995-67 Typical Flow (10.72 SFC@50 F.): 5% Cottonseed Oil Stearin | 7% CSO Stearin 93% EIE Cottonseed Oil Base Oil 5995-67 Typical Flow (10.72 SFC@50 F.): 7% Cottonseed Oil Stearin |
| MDP (° F.) | 82.40 | 82.22 | 82.94 | 82.49 |
| SFC @ 50° F. | 10.72 | 12.84 | 13.98 | 15.25 |
| SFC @ 68° F. | 3.49 | 3.99 | 4.20 | 4.17 |
| SFC @ 70° F. | 3.07 | 3.41 | 3.58 | 3.97 |
| SFC @ 77° F. | 2.30 | 2.50 | 2.69 | 2.66 |
| SFC @ 80° F. | 2.01 | 2.30 | 2.10 | 2.17 |

TABLE 6-continued

| | | | | |
|---|---|---|---|---|
| SFC @ 86° F. | 1.38 | 1.48 | 1.29 | 1.56 |
| SFC @ 92° F. | 0.49 | 0.59 | 0.71 | 0.86 |
| SFC @ 92° F. | 0.30 | 0.25 | 0.44 | 0.17 |
| SFC @ 104° F. | 0.50 | 0.05 | 0.00 | 0.14 |
| C16:0 sn-2 | 19.35 | | | |

| | Regular Flows 11.97 SFC@50 F. Start | | | |
|---|---|---|---|---|
| Analysis | NO ADD EIE DEOD CSO Larqe Bench 5995-105 | 3% CSO Stearin 97% EIE Cottonseed Oil Base Oil 5995-105 Typical Flow (11.97 SFC@50 F.): 3% Cottonseed Oil Stearin | 5% CSO Stearin 95% EIE Cottonseed Oil Base Oil 5995-105 Typical Flow (11.97 SFC@50 F.): 5% Cottonseed Oil Stearin | 7% CSO Stearin 93% EIE Cottonseed Oil Base Oil 5995-105 Typical Flow (11.97 SFC@50 F.): 7% Cottonseed Oil Stearin |
| MDP (° F.) | 81.86 | 82.94 | 82.94 | 84.56 |
| SFC @ 50° F. | 11.97 | 14.59 | 15.94 | 16.99 |
| SFC @ 68° F. | 4.19 | 4.31 | 4.77 | 5.06 |
| SFC @ 70° F. | 3.78 | 3.95 | 4.05 | 4.21 |
| SFC @ 77° F. | 2.60 | 2.71 | 2.83 | 2.75 |
| SFC @ 80° F. | 2.42 | 2.29 | 2.42 | 2.19 |
| SFC @ 86° F. | 1.67 | 1.70 | 1.74 | 1.66 |
| SFC @ 92° F. | 0.78 | 0.69 | 1.06 | 0.93 |
| SFC @ 92° F. | 0.56 | 0.49 | 0.56 | 0.39 |
| SFC @ 104° F. | 0.00 | 0.00 | 0.10 | 0.00 |
| C16:0 sn-2 | 20 | | | |

Table 7 shows the impact of cotton stearin addition post intraesterification for fast flow, i.e., ½ or 50% regular enzyme amount. As shown in Table 7, the addition of stearin provides increased MDP temperatures and increased SFC % at 50° F. under fast flow conditions as compared to an EIE cottonseed oil devoid of stearin under fast flow conditions. The ability to fine tune production of an EIE cottonseed oil having a specific predetermined target MDP temperature and SFC % at 50° F. is useful to meet the needs of manufacturers of margarines and spreads.

Table 8 shows the impact of cotton stearin addition post intraesterification for fast flow, i.e., ¼ or 25% regular enzyme amount. As shown in Table 8, the addition of stearin provides increased SFC % at 50° F. under double fast flow conditions as compared to an EIE cottonseed oil devoid of stearin under double fast flow conditions. As noted above, the ability to fine tune production of an EIE cottonseed oil having a specific predetermined target MDP temperature and SFC % at 50° F. is useful to meet the needs of manufacturers of margarines and spreads.

TABLE 7

| | Fast Flow (½ regular enzyme amount) 10.45 SFC @ 50° F. Start | | | |
|---|---|---|---|---|
| Analytical | NO ADD EIE DEOD CSO Large Bench Collect 1 Fast Flow 5995-110 | 3% CSO Stearin 97% EIE Cottonseed Oil Base Oil 5995-110 Fast Flow (10.45 SFC@50 F.):3% Cottonseed Oil Stearin | 5% CSO Stearin 95% EIE Cottonseed Oil Base Oil 5995-110 Fast Flow (10.45 SFC@50 F.):5% Cottonseed Oil Stearin | 7% CSO Stearin 93% EIE Cottonseed Oil Base Oil 5995-110 Fast Flow (10.45 SFC@50 F.):7% Cottonseed Oil Stearin |
| MDP (° F.) | 77.54 | 78.80 | 80.41 | 78.98 |
| SFC @ 50° F. | 10.45 | 10.73 | 11.14 | 11.44 |
| SFC @ 68° F. | 3.00 | 3.25 | 3.37 | 3.28 |
| SFC @ 70° F. | 2.71 | 3.01 | 2.76 | 3.06 |
| SFC @ 77° F. | 1.78 | 1.98 | 1.90 | 2.00 |
| SFC @ 80° F. | 1.36 | 1.52 | 1.51 | 1.77 |
| SFC @ 86° F. | 0.98 | 1.00 | 1.07 | 0.97 |
| SFC @ 92° F. | 0.58 | 0.47 | 0.48 | 0.45 |
| SFC @ 95° F. | 0.05 | 0.14 | 0.00 | 0.03 |
| SFC @ 104° F. | 0.00 | 0.00 | 0.00 | 0.00 |
| C 16:0 sn-2 | 12.29 | | | |

TABLE 8

| Double Fast Flow (1/4 regular enzyme amount) 4.39 SFC @ 50° Start | | | | |
|---|---|---|---|---|
| Analytical | NO ADD EIE DEOD CSO Large Bench Collect 1 Double-Fast Flow 5995-116 | 20% CSO Stearin 80% EIE Cottonseed Oil Base Oil 5995-116 Double-Fast Flow (4.39 SFC@50 F.):20% Cottonseed Oil Stearin | 25% CSO Stearin 75% EIE Cottonseed Oil Base Oil 5995-116 Double-Fast Flow (4.39 SFC@50 F.):25% Cottonseed Oil Stearin | 30% CSO Stearin 70% EIE Cottonseed Oil Base Oil 5995-116 Double-Fast Flow (4.39 SFC@50 F.):30% Cottonseed Oil Stearin |
| MDP (° F.) | 73.22 | 77.18 | 78.08 | 77.9 |
| SFC @ 50° F. | 4.39 | 9.34 | 11.59 | 14.34 |
| SFC @ 68° F. | 1.62 | 2.25 | 2.63 | 2.72 |
| SFC @ 70° F. | 1.55 | 2.01 | 2.22 | 2.55 |
| SFC @ 77° F. | 1.00 | 1.45 | 1.73 | 1.55 |
| SFC @ 80° F. | 0.84 | 1.08 | 1.30 | 1.39 |
| SFC @ 86° F. | 0.39 | 0.60 | 0.59 | 0.76 |
| SFC @ 92° F. | 0.10 | 0.00 | 0.00 | 0.00 |
| SFC @ 95° F. | 0.04 | 0.00 | 0.00 | 0.00 |
| SFC @ 104° F. | 0.00 | 0.00 | 0.00 | 0.00 |
| C 16:0 sn-2 | 2.67 | | | |

The following examples discuss the production of fat spreads in accordance with aspects of the invention. More specifically, 60% fat spreads using EIE Cottonseed Oil were processed to different degrees of reaction. The various fat spreads were analysed to determine the degree of reaction effects have on the crystallization and functionality of EIE cottonseed oil as a base oil in a spreads application. Two spread formulations that have cotton stearin added at different concentrations were produced and analysed to determine the effect of cotton stearin on the physical properties of the base oil.

60% fat spreads were produced on an Armfield votation unit, then stored at refrigerated temperatures. Characterization testing was performed on the spreads over a set period of time.

Samples Produced

Spread #1 (5995-105 Regular Flow)

Spread #2 (5995-67 Regular Flow)

Spread #3 (5995-110 Fast Flow)

Spread #4 (5995-110 Fast Flow+5% Cotton Stearin)

Spread #5 (5995-116 2× Fast Flow+25% Cotton Stearin)

Spread #6 Control (75% SBO/25% 74-325-0)

Batch size=4.5 kg for each spread

Sample Collection

Spreads were processed on an Armfield votation unit.

Spreads were collected in 16-ounce cup containers, filled ⅔ full of each spread. These samples were used for the characterization work on the spreads for the duration of the study. In addition, each spread was placed in 4-ounce containers to be used for sensory evaluation over the duration of the study.

Duration of Study 0 week, 1 week, 2 weeks, 4 weeks, and 8 weeks were the time points for testing the spreads after initial production. Protocol for testing spread samples: static texture data was collected on spread right out of fridge, then the spread sample was left out for 1 hour then put back into fridge to recrystallize, and texture data was collected on cycled spread the next day.

Analysis

Spread base: 50 g of spread base (oil blend, distilled monoglycerides, lecithin) was pulled before adding aqueous phase to create an emulsion. On each spread base run the following: SFC, MDP, FAC, ROC.

Spreads: Texture Analyzer method using TA-55 5 mm Puncture Probe, Sensory Evaluation, Microscopy.

Table 9 shows the formulation for spreads #1 through #6, wherein spreads #1 through #5 were EIE CSO produced in accordance with aspects of the present invention, and spread #6 was a control.

TABLE 9

| | % | 4.5 kg Batch | | |
|---|---|---|---|---|
| Spread #1 (5995-105 regular flow) | | | | |
| Oil Phase (60%) | | | | |
| EIE Cottonseed Oil (lot 5995-105 Regular Flow) | 59.30 | 2.6685 | kg | |
| Distilled Monoglyceride | 0.50 | 0.0225 | kg | =22.5 g |
| Soy Lecithin | 0.20 | 0.009 | kg | =9 g |
| | 60.00 | | | |
| Water Phase (40%) | | | | |
| Water | 39.00 | 1.755 | kg | |
| Salt | 1.00 | 0.045 | kg | =45 g |
| | 40.00 | | | |

TABLE 9-continued

| | % | 4.5 kg Batch | |
|---|---|---|---|
| Spread #2 (5995-67 regular flow) | | | |
| Oil Phase (60%) | | | |
| EIE Cottonseed Oil (lot 5995-67 Regular Flow) | 59.30 | 2.6685 kg | |
| Distilled Monoglyceride | 0.50 | 0.0225 kg | =22.5 g |
| Soy Lecithin | 0.20 | 0.009 kg | =9 g |
| | 60.00 | | |
| Water Phase (40%) | | | |
| Water | 39.00 | 1.755 kg | |
| Salt | 1.00 | 0.045 kg | =45 g |
| | 40.00 | | |
| Spread #3 (5995-110 fast flow) | | | |
| Oil Phase (60%) | | | |
| EIE Cottonseed Oil (lot 5995-110 Fast Flow) | 59.30 | 2.6685 kg | |
| Distilled Monoglyceride | 0.50 | 0.0225 kg | =22.5 g |
| Soy Lecithin | 0.20 | 0.009 kg | =9 g |
| | 60.00 | | |
| Water Phase (40%) | | | |
| Water | 39.00 | 1.755 kg | |
| Salt | 1.00 | 0.045 kg | = 45 g |
| | 40.00 | | |
| Spread #4 (5995-110 fast flow + 5% Cotton Stearin) | | | |
| Oil Phase (60%) | | | |
| EIE Cottonseed Oil (lot 5995-110 Fast Flow) | 56.335 | 2.535075 kg | |
| Cotton Stearin (lot) | 2.965 | 0.133425 kg | =133.425 g |
| Distilled Monoglyceride | 0.50 | 0.0225 kg | =22.5 g |
| Soy Lecithin | 0.20 | 0.009 kg | =9 g |
| | 60.00 | | |
| Water Phase (40%) | | | |
| Water | 39.00 | 1.755 kg | |
| Salt | 1.00 | 0.045 kg | =45 g |
| | 40.00 | | |
| Spread #5 (5995-116 2x fast flow + 25% Cotton Stearin) | | | |
| Oil Phase (60%) | | | |
| EIE Cottonseed Oil (lot 5995-116 2x Fast Flow) | 44.475 | 2.001375 kg | |
| Cotton Stearin (lot) | 14.825 | 0.667125 kg | =667.125 g |
| Distilled Monoglyceride | 0.50 | 0.0225 kg | =22.5 g |
| Soy Lecithin | 0.20 | 0.009 kg | =9 g |
| | 60.00 | | |
| Water Phase (40%) | | | |
| Water | 39.00 | 1.755 kg | |
| Salt | 1.00 | 0.045 kg | =45 g |
| | 40.00 | | |
| Spread #6 Control (75% SBO/25% 74-325-0) | | | |
| Oil Phase (60%) | | | |
| Soybean Oil | 44.475 | 2.001375 kg | |
| IE Palm Stearin/Palm Kernel Oil | 14.825 | 0.667125 kg | =667.125 g |
| Distilled Monoglyceride | 0.50 | 0.0225 kg | =22.5 g |
| Soy Lecithin | 0.20 | 0.009 kg | =9 g |
| | 60.00 | | |
| Water Phase (40%) | | | |
| Water | 39.00 | 1.755 kg | |
| Salt | 1.00 | 0.045 kg | =45 g |
| | 40.00 | | |

Figure 4:
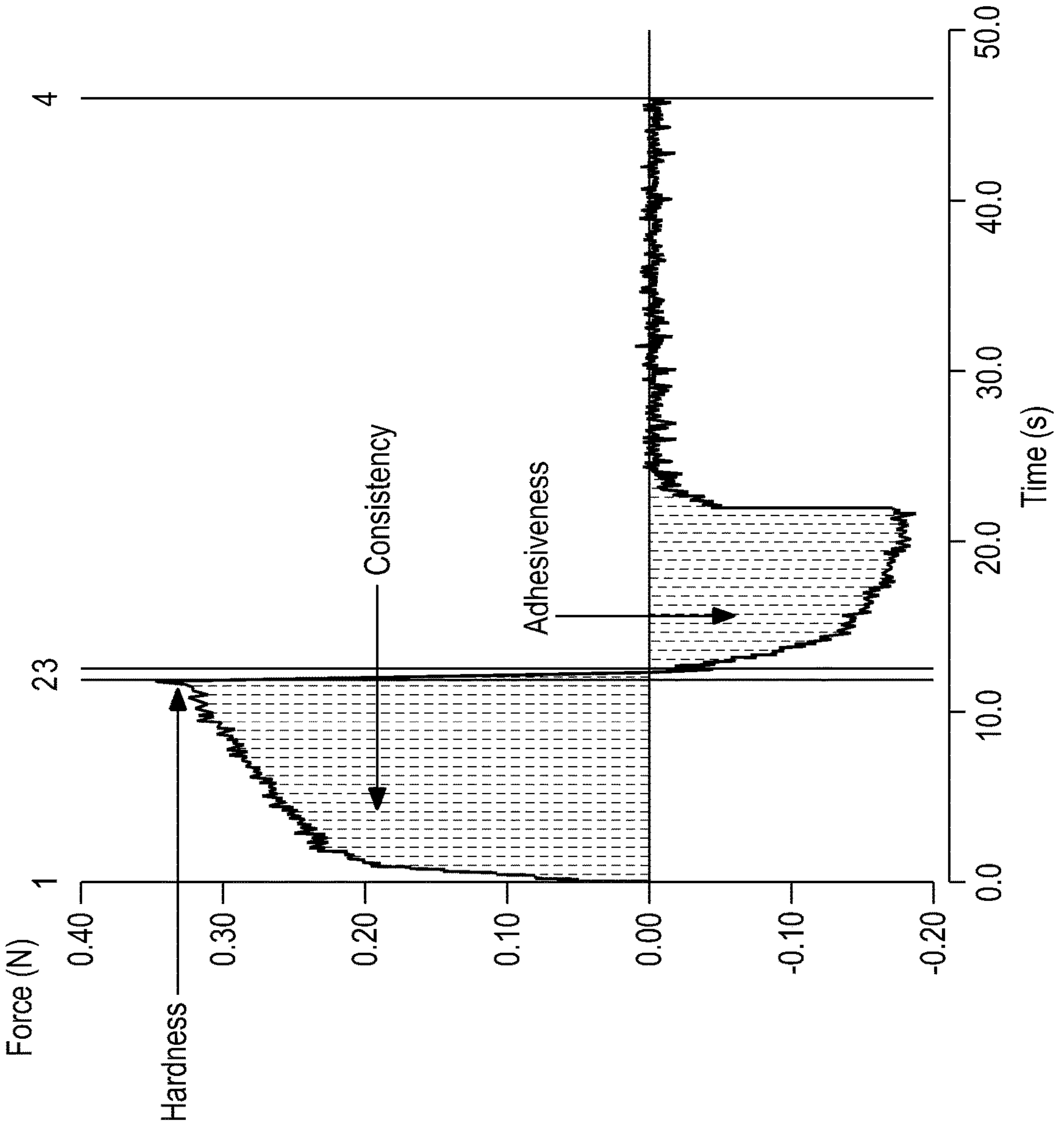
FIG. 4 shows a model graph for the texture analysis of a spread.

Table 10 shows an analysis for spread oil phase sample spreads #1 through #6, identified in Table 9. As shown in Table 10, spreads #1 through #5, produced using intraesterified cottonseed oil in accordance with aspects of the present invention, have SFC % at 50° F. that is close to spread #6 produced using 75% soybean oil (SBO)/25% interesterified palm stearin/palm kernel oil 74-325-0). For example, spread #1 had SFC % at 50° F. of 12.00%, which is close to spread #6, which had SFC % at 50° F. of 14.60%. The regular flow rate (referred to as typical flow in Table 10) used for spreads #1 and #2 was the same regular flow rate used for spread #6.

curves (sharp & narrow or shallow & extended) and the minima of the adhesion peak shown in FIG. 4. During probe withdrawal, if the sample exhibited more adhesion tendency (sample+probe) than cohesion (sample+sample), then the profile of negative curve will be shallow and extended and the negative curve area will be small. The larger the negative curve area, the higher the brittle nature and the lower of its spreadability of the spread. For comparable negative curve areas, a "sharp and narrow" profile represents brittle nature and a "shallow and extended" profile represents relative ease of spreadability of the spread.

TABLE 10

| | Spread Oil Phase Samples (contain base oil blend, distilled monoglyceride, and soy lecithin) | | | | | |
|---|---|---|---|---|---|---|
| Analysis | Spread #1 EIE CSO Typical Flow Lot# 11671 | Spread #2 EIE CSO Typical Flow (Different Batch) Lot# 11672 | Spread #3 EIE CSO Fast Flow Lot# 11673 | Spread #4 EIE CSO Fast Flow + 5% Cotton Stearine Lot# 11674 | Spread #5 EIE CSO Double Fast Flow + 25% Cotton Stearine Lot# 11675 | Spread #6 Control 75% SBO/ 25% EIE Palm/PK Lot# 11676 |
| SFC @ 50° F | 12.00 | 11.05 | 10.45 | 11.00 | 11.98 | 14.60 |
| SFC @ 70° F | 3.49 | 3.79 | 3.11 | 3.27 | 3.15 | 6.75 |
| SFC @ 80° F | 3.19 | 2.63 | 2.20 | 2.01 | 2.02 | 4.47 |
| SFC @ 92° F | 1.09 | 0.85 | 0.36 | 0.42 | 0.07 | 2.15 |
| SFC @ 104° F. | 0.25 | 0.21 | 0.02 | 0.13 | 0 | 0 |
| Mettler Drop Point (° C.) | 28.3 | 28.4 | 26.8 | 26.9 | 26.4 | 30.6 |
| Mettler Drop Point (° F.) | 82.94 | 83.12 | 80.24 | 80.42 | 79.52 | 87.08 |
| Butyric C4:0 | 0.00 | 0.00 | 0.00 | 0.00 | 0.00 | 0.00 |
| Caproic C6:0 | 0.00 | 0.00 | 0.00 | 0.00 | 0.00 | 0.02 |
| Caprylic C8:0 | 0.00 | 0.01 | 0.01 | 0.01 | 0.01 | 0.38 |
| Capric C10:0 | 0.00 | 0.00 | 0.00 | 0.00 | 0.00 | 0.35 |
| Lauric C12:0 | 0.02 | 0.01 | 0.01 | 0.01 | 0.01 | 4.78 |
| Myristic C14:0 | 0.89 | 0.81 | 0.89 | 0.87 | 0.82 | 1.90 |
| Palmitic C16:0 | 23.97 | 23.35 | 24.07 | 24.75 | 28.80 | 17.80 |
| Palmitoleic C16:1 | 0.59 | 0.54 | 0.59 | 0.58 | 0.53 | 0.07 |
| Stearic C18:0 | 3.06 | 3.16 | 3.03 | 3.03 | 2.98 | 4.70 |
| Total C18:1 trans FA | 0.08 | 0.06 | 0.05 | 0.06 | 0.04 | 0.05 |
| Total C18:1 cis FA | 15.55 | 16.21 | 15.52 | 15.45 | 15.32 | 21.48 |
| Total C18:2 trans FA | 0.25 | 0.31 | 0.28 | 0.27 | 0.23 | 0.11 |
| Total C18 2 cis FA | 53.85 | 53.68 | 53.79 | 53.27 | 49.57 | 42.01 |
| Total C18:3 trans FA | 0.02 | 0.01 | 0.01 | 0.02 | 0.00 | 0.13 |
| Total C18:3cis FA | 0.27 | 0.28 | 0.24 | 0.19 | 0.21 | 5.49 |
| Arachidic C20:0 | 0.28 | 0.29 | 0.27 | 0.26 | 0.26 | 0.30 |
| Behenic C22:0 | 0.12 | 0.14 | 0.13 | 0.11 | 0.13 | 0.24 |
| Lignoceric C24:0 | 0.09 | 0.07 | 0.11 | 0.08 | 0.07 | 0.05 |
| Total trans FA | 0.35 | 0.38 | 0.33 | 0.35 | 0.28 | 0.28 |
| Total Saturated FAs | 28.39 | 27.80 | 28.51 | 29.10 | 33.05 | 30.38 |

The following procedure was used for texture analysis of food spread samples. Texture attributes of spread samples were measured by using Texture Analyzer TA.HDPlus equipped with a 5 mm cylindrical puncture probe (TA-55 5 mm). A test consisted of using a "Return to Start" test measured in compression to penetrate into a tub of product at a test speed of 2 mm/sec, to a depth of 10 mm. Three replicates were tested for each sample and the probe was wiped clean with a lint-free towel between each replicate. The "initial sample" represents measurements done on a product tub pulled from refrigerator (38° F.) and tested within 2 minutes of withdrawal.

FIG. 4 depicts a texture analysis model graph and parameter interpretation for a food spread. The following describes the model graph and parameter interpretation.

Firmness/Hardness (Force, g)—Maximum resistance to the penetration (height of peak 2 in FIG. 4). The higher the maximum resistance, i.e., height of peak 2, the higher is the firmness of the spread.

Spreadability/Adhesiveness (Force-time, g.s)—This characteristic is indicated primarily by the profile of the negative Consistency (Force-time, g.s)—This characteristic is indicated primarily by the profile of the resistance peak (smooth or jagged) and the area of the resistance peak. A smooth graph indicates product uniformity at different depths of container. Jaggedness indicates varying resistance to the descending probe stemming most likely from development of shear planes to relieve the buildup of internal stress.

Figure 5:
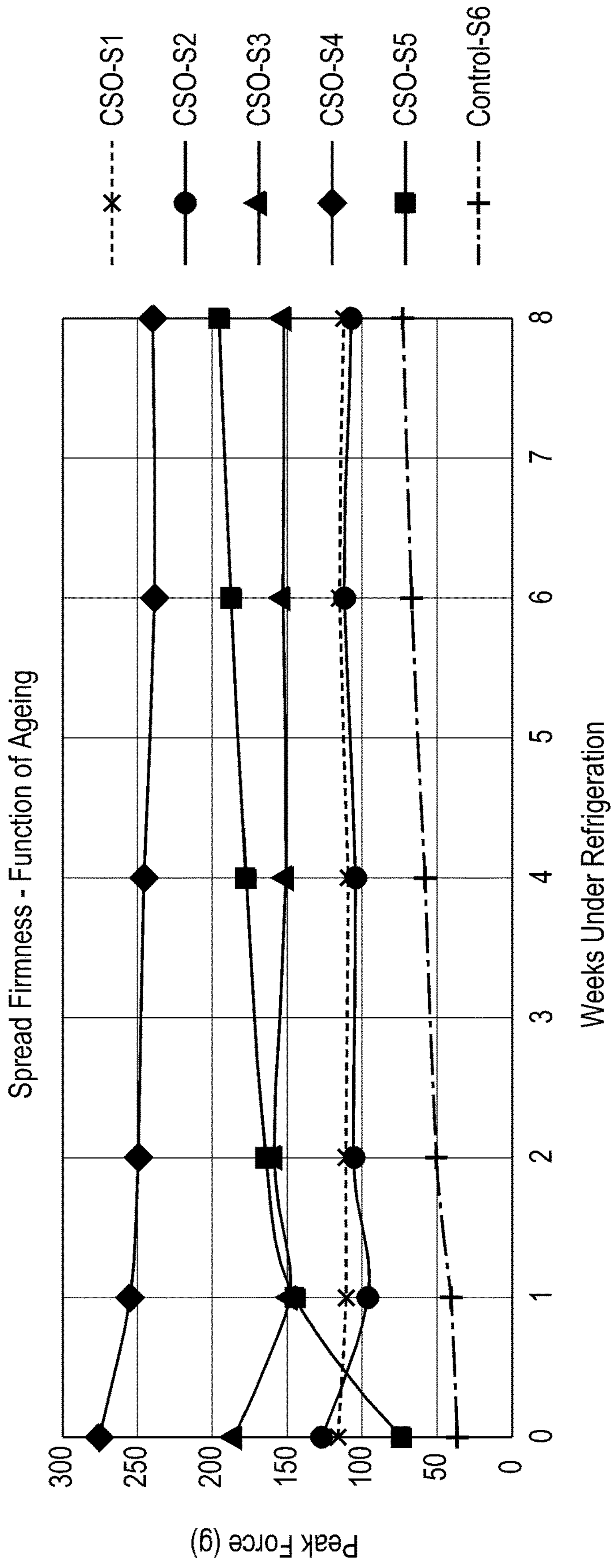
FIG. 5 is a graph showing spread firmness as a function of ageing for spreads comprising intraesterified cottonseed triglyceride product in accordance with aspects of the present invention as compared to a control spread comprising 75% soybean oil and 25% interesterified palm stearin/palm kernel oil, as characterized by peak force (g) versus time (weeks).

FIG. 5 is a graph showing spread firmness as a function of ageing for spreads comprising intraesterified cottonseed triglyceride product in accordance with aspects of the present invention as compared to a control spread comprising 75% soybean oil and 25% interesterified palm stearin/palm kernel oil, as characterized by peak force (g) versus time (weeks). As shown in FIG. 5, spreads #1 through #5 comprising intraesterified cottonseed triglyceride product had greater spread firmness from week zero (0) through week eight (8) than the control spread #6. Spread #1 exhibited the most consistency of spread firmness over the eight (8) week trial than the other spreads, followed closely by spread #2. At week zero (0), spreads #1 and #2 had spread firmness of about 110 peak force (g) and 125 peak force (g), respectively, whereas the control spread had spread firmness of about 40 peak force (g). At week eight (8), spreads #1 and #2 had spread firmness of about 110 peak force (g), whereas the control spread had spread firmness of about 70 peak force (g). Spreads #3, #4 and #5 demonstrate the impact of adding cotton stearin to the intraesterified cottonseed oil to increase spread firmness. Spreads #1 and #2 showed very consistent firmness throughout the aging study indicating that lot to lot intraesterified cottonseed oil demonstrates similar crystallization tendencies or characteristics. The consistency over the 8-week storage study of spread #1, spread #2 and spread #6 indicate that intraesterified cottonseed oil demonstrates similar crystallization behaviour to the of the interesterified palm/palm kernel basestock commonly used in margarine and spread manufacturing.

Figure 6:
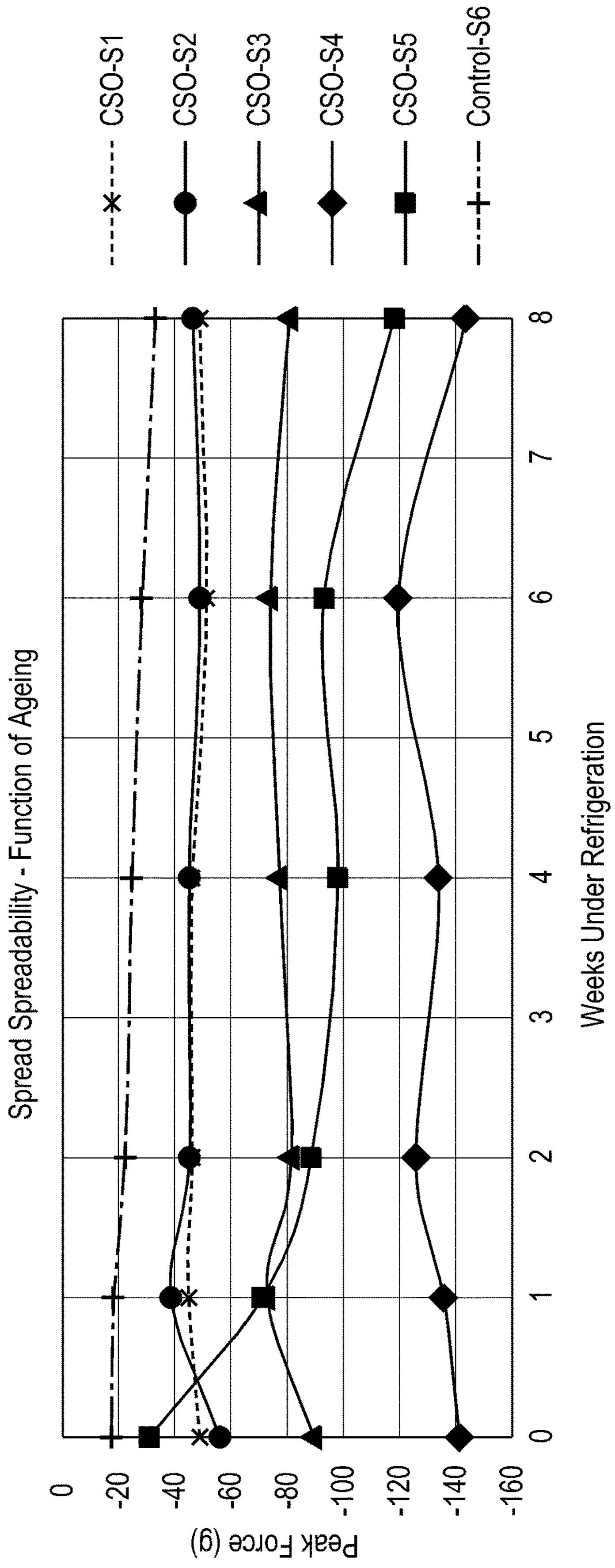
FIG. 6 is a graph showing spread spreadability as a function of ageing for spreads comprising intraesterified cottonseed triglyceride product in accordance with aspects of the present invention as compared to a control spread comprising 75% soybean oil and 25% interesterified palm stearin/palm kernel oil, as characterized by peak force (g) versus time (weeks).

FIG. 6 is a graph showing spread spreadability as a function of ageing for spreads comprising intraesterified cottonseed triglyceride product in accordance with aspects of the present invention as compared to a control spread comprising 75% soybean oil and 25% interesterified palm stearin/palm kernel oil, as characterized by peak force (g) versus time (weeks). Spread #1 exhibited the most consistency of spread firmness over the eight (8) week trial than the other spreads, followed closely by spread #2. At week zero (0), spreads #1 and #2 had spread spreadability of about −50 peak force (g) and −55 peak force (g), respectively, whereas the control spread had spread spreadability −20 peak force (g). At week eight (8), spreads #1 and #2 had spread spreadability of about −45 peak force (g) and −40 peak force (g), respectively, whereas the control spread #6 had spread spreadability of about −25 peak force (g). Spreads #1 and #2 demonstrate similar spreading characteristics to spread #6 over the course of the 8-week storage study. This data indicates that the post crystallization tendencies of the intraesterified cottonseed oil are similar to that common interesterified palm/palm kernel oil based spread commonly used in the margarine and spreads industry.

Figure 7:
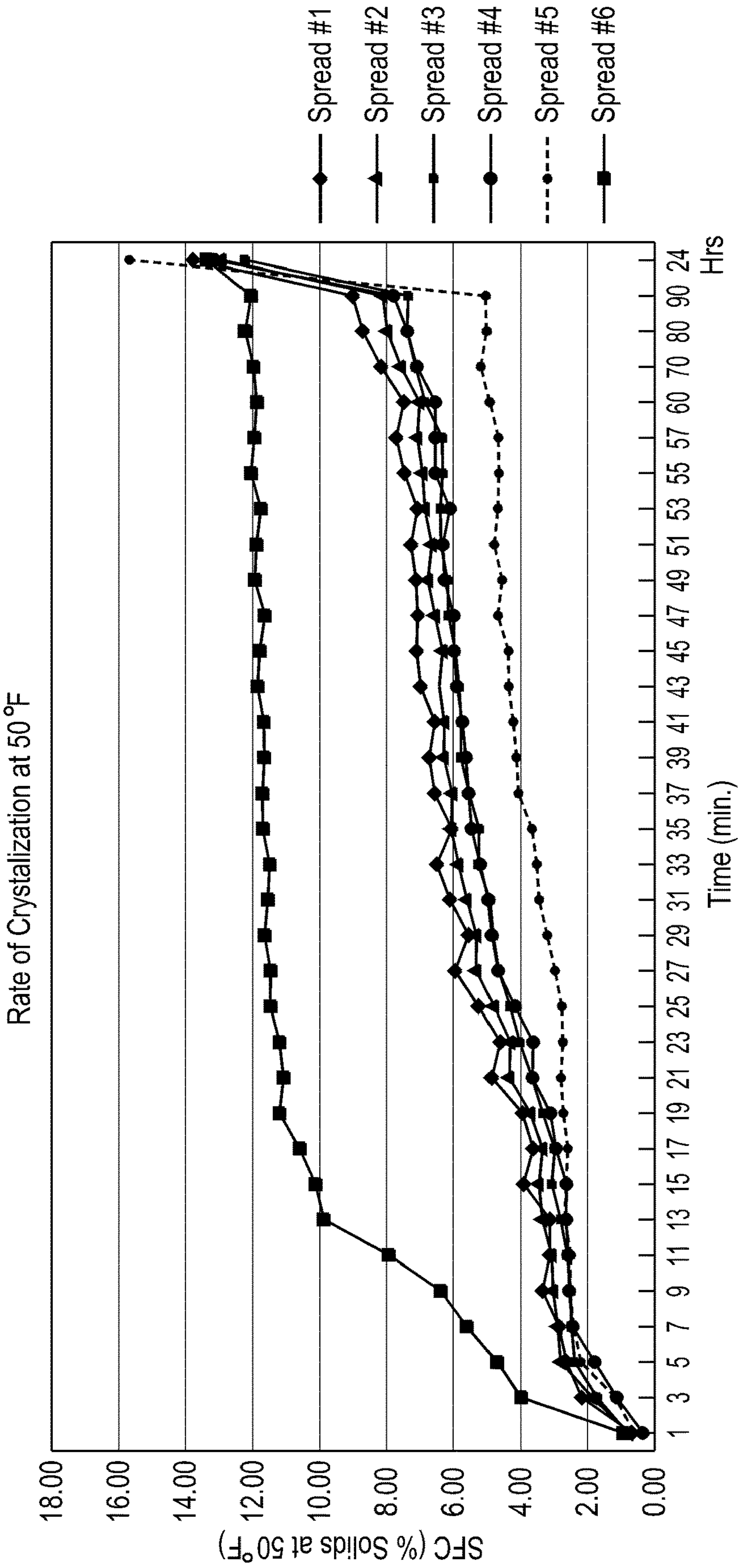
FIG. 7 is a graph showing rate of crystallization at 50° F. as characterized as SFC (% solids at 50° F.) as a function of time for spreads comprising intraesterified cottonseed triglyceride product in accordance with aspects of the present invention as compared to a control spread comprising 75% soybean oil and 25% interesterified palm stearin/palm kernel oil.

FIG. 7 is a graph showing rate of crystallization at 50° F. as characterized as SFC (% solids at 50° F.) as a function of time for spreads comprising intraesterified cottonseed triglyceride product (spreads #1 through #5) in accordance with aspects of the present invention as compared to a control spread comprising 75% soybean oil and 25% interesterified palm stearin/palm kernel oil (spread #6). Spreads #1 through #5 showed similar crystallization rates, demonstrating that intraesterified cottonseed oil with or without cotton stearin adjustment equilibrates similar to that of the spread #6 basestock after 24 hours. This data indicates that within 24 hours intraesterified cottonseed oil demonstrates similar crystallization characteristics to a spread made with interesterified palm/palm kernel oil commonly used in margarine and spread production.

Figure 8:
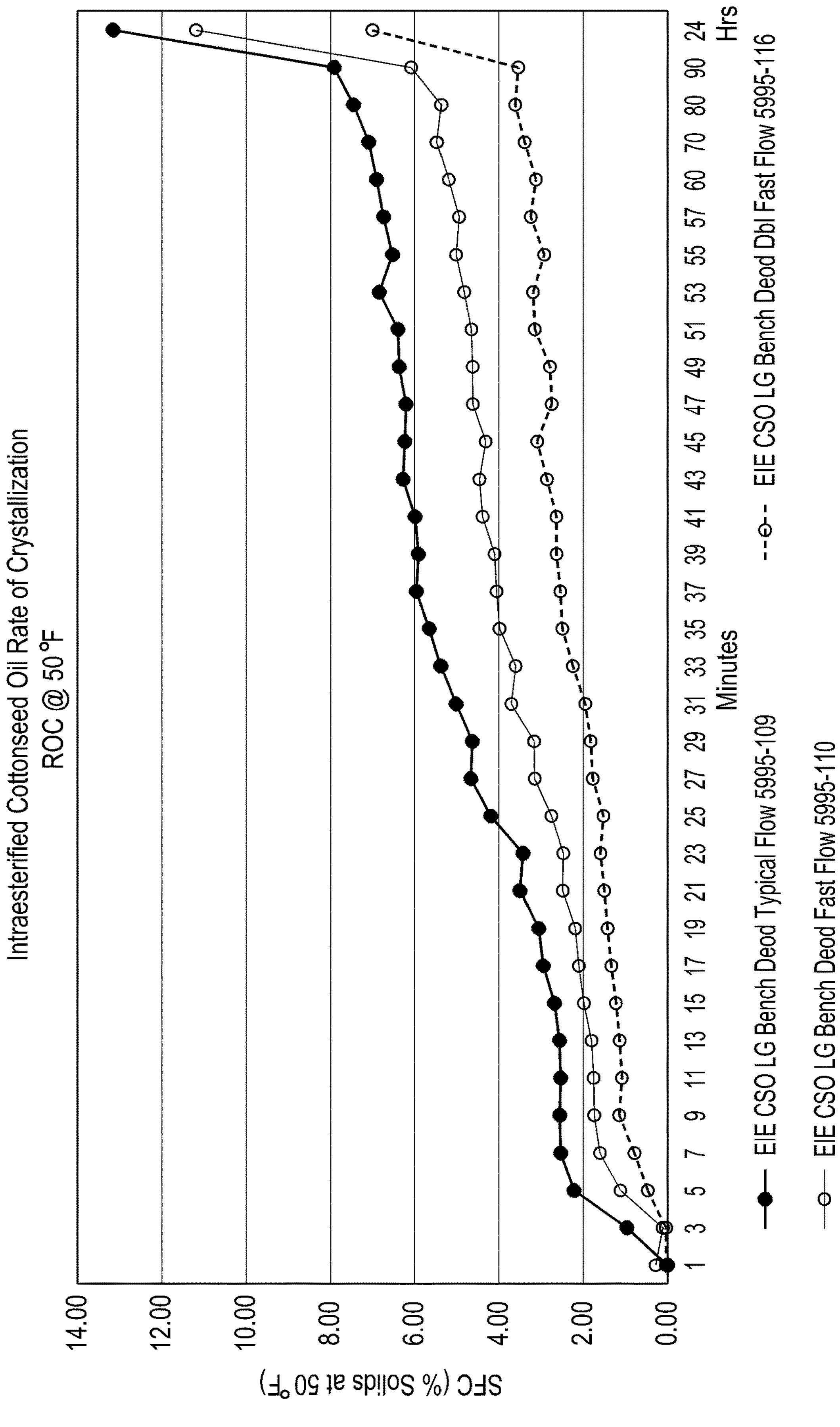
FIG. 8 is a graph showing rate of crystallization at 50° F. as characterized as SFC (% solids at 50° F.) as a function of time for spread basestocks comprising intraesterified cottonseed triglyceride product in accordance with aspects of the present invention, wherein the spread basestocks were deodorized and did not contain cotton stearin.

FIG. 8 is a graph showing rate of crystallization at 50° F. as characterized as SFC (% solids at 50° F.) as a function of time for intraesterified cottonseed triglyceride product in accordance with aspects of the present invention. FIG. 8 shows the impact of flow rates on rate of crystallization. The intraesterified cottonseed triglyceride products identified in FIG. 8, i.e., EIE CSO LG Bench Deod Typical Flow 5995-109 (typical flow is also referred to herein as regular flow), EIE CSO LG Bench Deod Fast Flow 5995-110, and EIE CSO LG Bench Deod Dbl (Double) Fast Flow 5995-116, were deodorized and did not contain cotton stearin. As shown in FIG. 8, rate of crystallization characteristics will vary depending on the degree of intraesterification that takes place a result of the flow rate and residence time. The data shown in FIG. 8 further indicates that intraesterified cottonseed oil in accordance with aspects of the present invention can be successfully used as feedstock or basestock in margarine or spread production.

The addition of saturated fat, e.g., in the form of cotton stearin, was found to increase ability to fine tune characteristics of the product comprising intraesterified cottonseed oil.

The addition of cotton stearin improved spread resiliency to thaw-freeze cycle.

In accordance with aspects of the invention, cotton stearin may be added before intraesterification or after intraesterification of the basestock.

Different crops of natural cottonseed oil can have a different amount of saturated components in the triglyceride, e.g., different total palmitic acid and total saturates. For example, over a three (3) year period, different crops of natural cottonseed oil have been observed that have saturated components varying from about 27.6 to about 24.9% by weight. In an aspect of the present invention, the addition of cotton stearin prior to enzymatic intraesterification may be used to adjust saturate content to ensure greater consistency in feedstock.

In accordance with aspects of the present invention, enzyme half-life can be improved by re-bleaching and/or re-deodorizing RBD oil to improve oil quality prior to intraesterification of the RBD oil.

Those skilled in the art having the benefit of the present disclosure will recognize that the above features disclosed herein provides processes and compositions that do not have the disadvantages of conventional processes and compositions.

Those having skill in the art, with the knowledge gained from the present disclosure, will recognize that various changes can be made to the disclosed processes in attaining these and other advantages, without departing from the scope of the present disclosure. As such, it should be understood that the features of the disclosure are susceptible to modifications and/or substitutions. The specific embodiments illustrated and described herein are for illustrative purposes only, and not limiting of the invention as set forth in the appended claims.

What is claimed is:

1. A composition comprising a 1,3-selective enzymatic intraesterified oil product having a greater USU content than the oil from which it was derived, the oil having a greater SUS content than USU content, wherein the 1,3-selective enzymatic intraesterified oil product is a 1,3-selective enzymatic intraesterified cottonseed oil product.

2. The composition of claim 1, wherein the oil from which the 1,3-selective enzymatic intraesterified oil product is derived is a regular cottonseed oil defined by the U being primarily linoleic acid and the S being palmitic acid.

3. The composition of claim 1, wherein the 1,3-selective enzymatic intraesterified oil product has solid fat content at 50° F. that is greater than the oil from which it was derived.

4. The composition of claim 3, wherein the 1,3-selective enzymatic intraesterified oil product has a solid fat content at 50° F. that is at least ten (10) times greater than the oil from which it was derived.

5. The composition of claim 3, wherein the 1,3-selective enzymatic intraesterified oil product has a solid fat content of at least 4% at 50° F.

6. The composition of claim 3, wherein the 1,3-selective enzymatic intraesterified oil product has a solid fat content of at least 7% at 50° F.

7. The composition of claim 3, wherein the 1,3-selective enzymatic intraesterified oil product has a solid fat content of at least 9% at 50° F.

8. The composition of claim 3, wherein the 1,3-selective enzymatic intraesterified oil product has a solid fat content of at least 9.5% at 50° F.

9. The composition of claim 3, wherein the 1,3-selective enzymatic intraesterified oil product comprises linoleic acid.

10. The composition of claim 3, wherein the 1,3-selective enzymatic intraesterified oil product is an intraesterified cottonseed oil.

11. The composition of claim 3, wherein the 1,3-selective enzymatic intraesterified oil product has re-esterified fatty acids derived solely from cottonseed oil.

12. The composition of claim 1, wherein the 1,3-selective enzymatic intraesterified oil product has a melting temperature of at least 75° F.

13. The composition of claim 1, wherein the 1,3-selective enzymatic intraesterified oil product has at least 25% more palmitic acid esterified to the second carbon of the glycerol than the oil from which it was derived.

14. The composition of claim 1, wherein the 1,3-selective enzymatic intraesterified oil product has at least 12% palmitic acid esterified to the second carbon of the glycerol.

15. The composition of claim 1 further comprising an amount of stearin present at 3% by weight or more.

* * * * *